United States Patent
Pack et al.

(10) Patent No.: US 10,964,017 B2
(45) Date of Patent: Mar. 30, 2021

(54) DEEP LEARNING FOR ARTERIAL ANALYSIS AND ASSESSMENT

(71) Applicant: General Electric Company, Schenectady, NY (US)

(72) Inventors: Jed Douglas Pack, Glenville, NY (US); Peter Michael Edic, Albany, NY (US); Xin Wang, Clifton Park, NY (US); Xia Li, Niskayuna, NY (US); Prem Venugopal, Clifton Park, NY (US); James Vradenburg Miller, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 177 days.

(21) Appl. No.: 16/192,551

(22) Filed: Nov. 15, 2018

(65) Prior Publication Data

US 2020/0160509 A1 May 21, 2020

(51) Int. Cl.
| | | |
|---|---|---|
| *G06T 7/00* | (2017.01) |
| *G16H 50/20* | (2018.01) |
| *G16H 30/40* | (2018.01) |
| *G06N 3/08* | (2006.01) |

(52) U.S. Cl.
CPC .......... *G06T 7/0012* (2013.01); *G06N 3/084* (2013.01); *G16H 30/40* (2018.01); *G16H 50/20* (2018.01); *G06T 2207/10081* (2013.01); *G06T 2207/30104* (2013.01)

(58) Field of Classification Search
USPC ..... 382/128, 130–132, 155–156; 706/15, 20, 706/25
See application file for complete search history.

(56) References Cited

U.S. PATENT DOCUMENTS

| | | | |
|---|---|---|---|
| 8,068,894 B2 * | 11/2011 | Huizenga | A61B 5/055 |
| | | | 382/276 |
| 9,349,178 B1 | 5/2016 | Itu et al. | |
| 9,700,219 B2 | 7/2017 | Sharma et al. | |
| 9,968,257 B1 * | 5/2018 | Burt | A61B 5/7267 |
| 10,258,244 B2 * | 4/2019 | Sharma | G06K 9/46 |
| 10,463,336 B2 * | 11/2019 | Itu | G06T 7/11 |
| 10,600,185 B2 * | 3/2020 | Yang | G06T 7/187 |
| 10,607,114 B2 * | 3/2020 | Novak | A61B 8/5207 |
| 2013/0132054 A1 * | 5/2013 | Sharma | G16B 5/00 |
| | | | 703/9 |
| 2013/0226003 A1 | 8/2013 | Edic et al. | |
| 2014/0005535 A1 | 1/2014 | Edic et al. | |

(Continued)

OTHER PUBLICATIONS

European application 19209284.9 filed Nov. 14, 2019—Search Report dated Feb. 14, 2020, 10 pages.

(Continued)

*Primary Examiner* — Ishrat I Sherali

(57) ABSTRACT

The present disclosure relates to training one or more neural networks for vascular vessel assessment using synthetic image data for which ground-truth data is known. In certain implementations, the synthetic image data may be based in part, or derived from, clinical image data for which ground-truth data is not known or available. Neural networks trained in this manner may be used to perform one or more of vessel segmentation, decalcification, Hounsfield unit scoring, and/ or estimation of a hemodynamic parameter.

12 Claims, 5 Drawing Sheets

(56) References Cited

U.S. PATENT DOCUMENTS

| | | |
|---|---|---|
| 2014/0073976 A1 | 3/2014 | Fonte et al. |
| 2014/0073977 A1 | 3/2014 | Grady et al. |
| 2015/0112182 A1* | 4/2015 | Sharma ............... A61B 5/7282 600/408 |
| 2017/0105694 A1* | 4/2017 | Grass .................... A61B 6/507 |
| 2017/0325769 A1 | 11/2017 | Venugopal et al. |
| 2017/0325770 A1 | 11/2017 | Edic et al. |
| 2018/0315182 A1 | 11/2018 | Rapaka |
| 2019/0066281 A1* | 2/2019 | Zheng .................. G06N 3/0454 |
| 2019/0205606 A1* | 7/2019 | Zhou .................... G06N 3/0445 |
| 2019/0336096 A1* | 11/2019 | Itu ........................ G06N 3/08 |

OTHER PUBLICATIONS

Lopez-Linares Roman Karen et al: "3D Pulmonary Artery Segmentation from CTA Scans Using Deep Learning with Realistic Data Augmentation", Sep. 12, 2018 (Sep. 12, 2018), 12th European Conference on Computer Vision, ECCV 2012; [Lecture Notes in Computer Science], Springer Berlin Heidelberg, Berlin, Heidelberg, pp. 225-237, XP047526341.

\* cited by examiner

DEEP LEARNING FOR ARTERIAL ANALYSIS AND ASSESSMENT

TECHNICAL FIELD

The subject matter disclosed herein relates to the use of deep-learning approaches for vascular analyses.

BACKGROUND

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

One area of clinical interest in which non-invasive imaging may be employed is in assessing blood flow in vessels. For example, such image data may be used in evaluating chronic blockages, which can restrict blood flow and impact downstream tissue (e.g., blood flow to myocardium or brain tissue). Such information may also be useful in assessing the risk of heart attacks and stroke, which are acute events that can result from such conditions. Using image data to diagnose such conditions can, therefore, help prevent such acute events and improve the health of those with chronic blood flow restrictions.

Currently, as in many processing-intensive techniques, there are tradeoffs between the use of three-dimensional anatomical modeling and complex three-dimensional fluid dynamics modeling techniques based on such imaging and vascular analysis approaches, respectively, and the computational time and resources that may be required to implement such approaches. Conversely, use of less complex, or dimensionally-reduced, modeling approaches, though less computationally intensive, may provide lower accuracy and/or reduced predictive benefit.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method is provided for processing a vascular image volume. In accordance with this embodiment, one or more vascular image volumes are acquired using an imaging system. The one or more vascular image volumes are provided to one or more neural networks. The one or more neural networks are trained using at least one or more synthetic images to perform one or more of: segmenting one or more vessels within the vascular image volumes; removing the effects of calcium in all or part of the vascular image volumes; determining a contrast level for one or more sections of the segmented vessels; or deriving one or more hemodynamic parameters for all or part of the segmented vessels.

In a further embodiment, an imaging system is provided. In accordance with this embodiment, the imaging system comprises: a memory encoding processor-executable routines and a processing component configured to access the memory and execute the processor-executable routines. The routines, when executed by the processing component, cause the processing component to: acquire one or more vascular image volumes and provide the one or more vascular image volumes to one or more neural networks. The one or more neural networks are trained using at least one or more synthetic images to perform one or more of: segmenting one or more vessels within the vascular image volumes; removing the effects of calcium in all or part of the vascular image volumes; determining a contrast level for one or more sections of the segmented vessels; or deriving one or more hemodynamic parameters for all or part of the segmented vessels.

In an additional embodiment, a method is provided for training one or more neural networks. In accordance with this embodiment a training data set comprising synthetic images having known ground-truth values for one or more features or parameters of interest is generated. Some or all of the synthetic images correspond to at least one of simplified anatomical models or vessel models derived from clinical images for which ground-truth values of the parameter of interest are not known. The one or more neural networks are trained using the training data set.

In a further embodiment, a method is provided for processing a vascular image volume. In accordance with this embodiment, one or more vascular image volumes are acquired using an imaging system. The one or more vascular image volumes are provided to one or more neural networks. The one or more neural networks are trained using at least one or more synthetic images to perform one or more of: segmenting one or more vessels within the vascular image volumes; removing the effects of calcium in all or part of the vascular image volumes; or determining a contrast level for one or more sections of the segmented vessels. One or more hemodynamic parameters are derived for all or part of segmented vessels using a computational fluid dynamics model.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
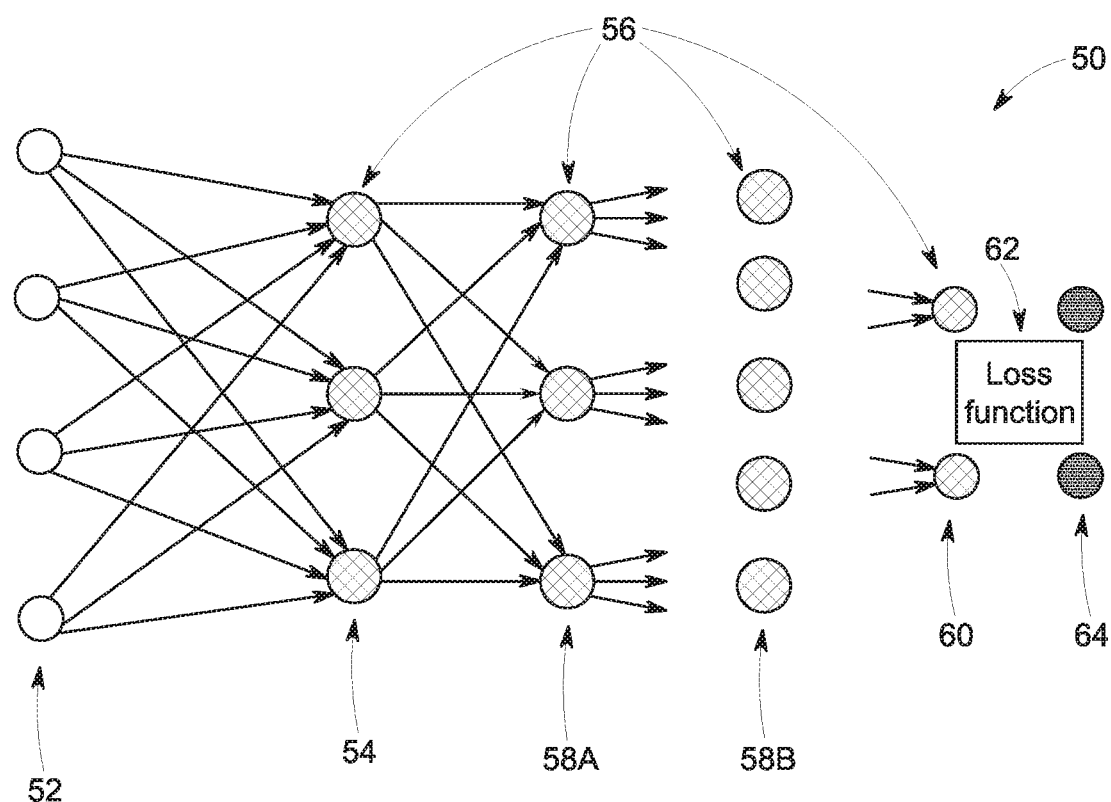
FIG. 1 depicts an example of an artificial neural network for training a deep-learning model, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While aspects of the following discussion are provided in the context of medical imaging, it should be appreciated that aspects of the disclosed techniques may be applicable to other contexts, and are thus not limited to such medical examples. Indeed, the provision of examples and explanations in such a medical context is only to facilitate explanation by providing instances of real-world implementations and applications, and should therefore not be interpreted as limiting the applicability of the present approaches with respect to other applicable uses, such as for non-destructive testing or baggage/cargo security screening.

Further, though CT and C-arm examples are primarily provided herein, it should be understood that the disclosed technique may be used in other imaging modality contexts where vascular imaging is performed. For instance, the presently described approach may also be employed on data acquired by other types of tomographic scanners including, but not limited to, positron emission tomography (PET) scanners, single photon emission computed tomography (SPECT) scanners, magnetic resonance imaging (MM) scanners, and/or combined implementations of such modalities.

By way of example, several imaging modalities, such as X-ray CT (e.g., multi-slice CT or volumetric CT) and X-ray C-arm systems (e.g., cone-beam CT), measure projections of an object or patient being scanned wherein the projections, depending on the technique, correspond to Radon transform data, fan-beam transform data, cone-beam transform data, or non-uniform Fourier transforms. Projections denote the data acquired during one or more specified time intervals corresponding to one or more angular orientations of the object or patient relative to the imaging system. In other contexts, the scan data may be emission type data (e.g., PET or SPECT data) or magnetic resonance data (e.g., MRI data) generated in response to magnetic fields and radiofrequency (RF) pulses. Tomographic reconstruction algorithms and related correction and calibration algorithms are employed in conjunction with these imaging modalities to generate useful volumetric images and/or models from raw measurements.

With this in mind, the techniques discussed herein utilize machine-learning approaches, such as may be embodied in one or more deep-learning algorithms, to perform one or more functions in a vascular imaging context. In certain of the implementations discussed herein, the deep-learning algorithms are trained using synthetic (e.g., simulated) images as training data, as opposed to clinical, real-world images or geometric constructs.

By way of example, deep-learning algorithms trained with synthetic image data, as described in greater detail below, may be trained to segment vessels, determine a true contrast level (e.g., Hounsfield unit (HU) scoring or estimation) along the length of segmented or unsegmented vessels (such as to address lack of apparent contrast in smaller vessels due to system resolution constraints), remove the effects of calcium in images, and/or determine or estimate a vascular parameter of interest, such as fractional flow reserve (FFR). As may be appreciated, though certain of these functions may be performed without the others, such as in a standalone manner to obtain various benefits, in practice certain of these functions may benefit from being performed in combination with the others. For example, segmentation and determination of true or accurate contrast levels may, in a vascular analysis context, be useful for determining blood flow velocity in an imaged region and/or otherwise provide local estimates of blood flow (as used herein, the term "local" may mean within an imaged region or portion of an imaged region, such as within or immediately around an organ, limb, or other limited anatomical region, as opposed to whole-body estimation or modeling). Both segmentation and lumen contrast estimation functions may benefit from removal of the effects of calcium, which may be viewed either as a separate or intertwined function. Furthermore, removing the effects of calcium from an image volume can add value for clinicians reviewing the image volume visually since calcium blooming can hinder the visualization of image features (e.g. fine structures proximal to the vasculature of interest).

The use of synthetic images for training one or more deep-learning algorithms, as discussed herein, is in contrast to the use of clinical images for such training purposes, which may involve either estimation of the ground-truth state or the acquisition of additional data that is representative of the ground-truth state and the registration of the additional data to the clinical image data to assemble the training data. As may be appreciated, such additional data acquisition may necessitate invasive approaches (such as to obtain ground-truth vascular parameters) and/or may otherwise introduce risks that might otherwise be avoided. For example, the internal boundaries of vessels can be determined using optical computed tomography (OCT) or intra-vascular ultrasound (IVUS). However, both techniques are invasive as they require insertion of a catheter, retrofitted with the appropriate sensing apparatus, into the vasculature of interest. Invasive approaches such as these incur additional risk to the patient.

With the preceding introductory comments in mind, some generalized information is provided both to indicate general context of the present disclosure and to facilitate understanding and explanation of certain technical concepts described herein.

For example, as noted above, deep-learning approaches may be employed with respect to improving or performing processing based on image data. The deep-learning aspects discussed herein may include approaches based on residual networks, generative adversarial networks, or other loss networks. In certain implementations, such deep-learning approaches may utilize neural networks to process image data or to perform operations based on such image data, which may include tomographic images, such as CT, PET, SPECT, C-arm, phase-contrast, and MR images. Neural networks as discussed herein may encompass deep neural networks, fully-connected networks, convolutional neural networks (CNNs), perceptrons, auto encoders, recurrent networks, wavelet filter banks based neural networks, or other neural network architectures. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine-learning techniques that employ mathematical representations of data and artificial neural network for learning. By way of example, deep-learning approaches may be characterized by their use of one or more algorithms to extract or model high-level abstractions of a type of data of interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data.

In general, the processing from one representation space to the next-level representation space can be considered as one 'stage' of the reconstruction process. Each stage of the reconstruction can be performed by separate neural networks or by different parts of one larger neural network. For example, as discussed herein, a single deep-learning network may be used to provide segmentation, contrast assessment, decalcification, or other steps as part of determining one or more local vascular properties.

As discussed herein, as part of the initial training of deep-learning processes to solve a particular problem, training data sets may be employed that have known initial values (e.g., input images, projection data, emission data, magnetic resonance data, and so forth) and known (i.e., ground truth) values for a final output of the deep-learning process. As discussed in greater detail below, in accordance with the present approach, the synthetic image data is used as training data, where the synthesized data is simulated or synthesized or derived from clinical image data and/or simple geometric constructs, but is distinct from the clinical image data. Further, due their synthetic nature, the synthetic training images discussed herein are associated with known ground-truth properties, without having to estimate such ground truths or perform additional invasive operations to derive such ground-truth properties. Such ground-truth information comprises one or more of vessel geometry (vessel length, vessel boundary representation, percentage of vessel narrowing at the position of the plaque, length of plaque, etc.), lumen contrast enhancement, adjacent plaques of varying composition, surrounding tissue, etc.

The training of a single stage may have known input values corresponding to one representation space and known output values corresponding to a next-level representation space. In this manner, the deep-learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep-learning algorithms, with the outputs then being compared to the outputs of the deep-learning algorithm to validate the prior training and/or to prevent over-training.

With the preceding in mind, FIG. 1 schematically depicts an example of an artificial neural network 50 that may be trained as a deep-learning model as discussed herein. In this example, the network 50 is multi-layered, with a training input 52 (e.g., synthetic image data) and multiple layers including an input layer 54, hidden layers 58A, 58B, and so forth, and an output layer 60 and the training target 64 present in the network 50. In certain implementations, the input layer 54 may also be characterized as or understood to be a hidden layer. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed function. The outputs of the final layer constitute the network output 60 which, in conjunction with a target image or parameter set 64, are used by loss or error function 62 to generate an error signal, which will be backpropagated to guide the network training.

The loss or error function 62 measures the difference between the network output and the training target. In certain implementations, the loss function may be the mean squared error (MSE) of the voxel-level values or partial-line-integral values and/or may account for differences involving other image features, such as image gradients or other image statistics. Alternatively, the loss function 62 could be defined by other metrics associated with the particular task in question, such as a softmax function or DICE value (where DICE refers to the ratio $$\frac{2*(A \cap B)}{|A|+|B|},$$

with A∩B denoting the intersection of regions A and B, and |•| denoting the area of the region.)

To facilitate explanation of the present approach using deep-learning techniques, the present disclosure primarily discusses these approaches in the context of a CT or C-arm systems. However, it should be understood that the following discussion may also be applicable to other image modalities and systems including, but not limited to, PET, SPECT, multi-spectral CT, phase-contrast imaging, and MRI, as well as to non-medical contexts or any context where tomographic reconstruction is employed to reconstruct an image.

Figure 2:
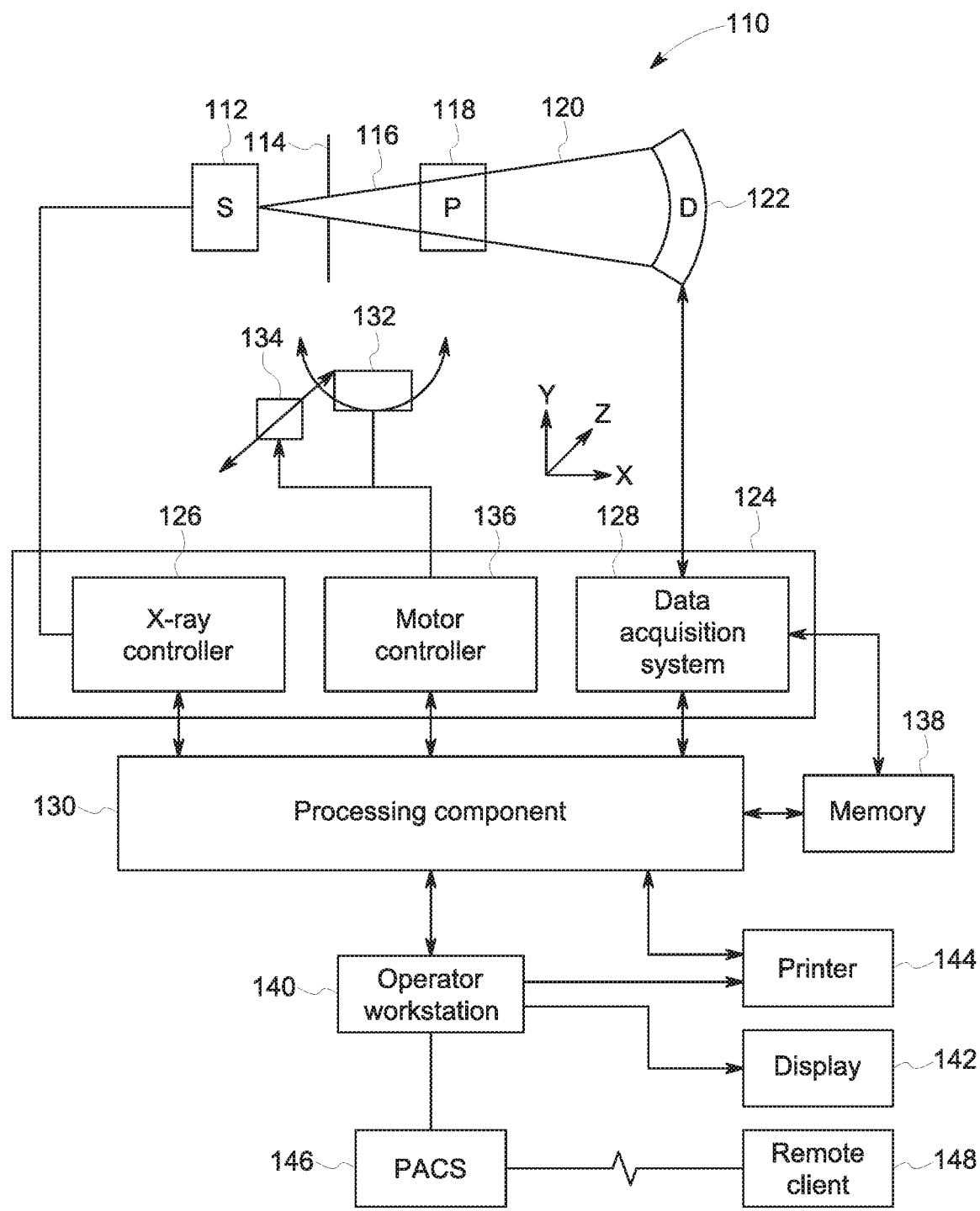
FIG. 2 is a block diagram depicting components of a computed tomography (CT) imaging system, in accordance with aspects of the present disclosure.

With this in mind, an example of an imaging system 110 (i.e., a scanner) is depicted in FIG. 2. In the depicted example, the imaging system 110 is a CT imaging system designed to acquire scan data (e.g., X-ray attenuation data) at a variety of views around a patient (or other subject or object of interest) and suitable for performing image reconstruction using tomographic reconstruction techniques. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images. Conversely, in a PET or SPECT embodiments, a toroidal radiation detector may be provided and a radioactive tracer injected into the patient is used as a radiation source. In the case of MRI, the measurements are samples in Fourier space and can either be applied directly as the input to the neural network or can first be converted to line integrals in sinogram space.

In the depicted example, the collimator 114 shapes or limits a beam of X-rays 116 that passes into a region in which a patient/object 118, is positioned. In the depicted example, the X-rays 116 are collimated to be a cone-shaped beam, i.e., a cone-beam, that passes through the imaged volume. A portion of the X-ray radiation 120 passes through or around the patient/object 118 (or other subject of interest) and impinges on a detector array, represented generally at reference numeral 122. Detector elements of the array produce electrical signals that represent the intensity of the incident X-rays 120. These signals are acquired and processed to reconstruct images of the features within the patient/object 118.

Source 112 is controlled by a system controller 124, which furnishes both power, and control signals for CT examination sequences. In the depicted embodiment, the system controller 124 controls the source 112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processing component 130 discussed below. Alternatively, in other embodiments, the digital-to-analog conversion may be performed by circuitry provided on the detector 122 itself. The system controller 124 may also execute various signal processing and filtration functions with regard to the acquired signals, such as for initial adjustment of dynamic ranges, interleaving of digital data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x,y-plane about the patient. It should be noted that the rotational subsystem 132 might include a gantry or C-arm upon which the respective X-ray emission and detection components are disposed. Thus, in such an embodiment, the system controller 124 may be utilized to operate the gantry or C-arm.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular regions of interest of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols and to process acquired data. For example, the system controller 124, via the systems and controllers noted above, may rotate a gantry supporting the source 112 and detector 122 about a subject of interest so that X-ray attenuation data may be obtained at one or more angular positions relative to the subject. In the present context, system controller 124 may also include signal processing circuitry, associated memory circuitry for storing programs and routines executed by the computer (such as routines for performing vascular property estimation techniques described herein), as well as configuration parameters, image data, and so forth.

In the depicted embodiment, the signals acquired and processed by the system controller 124 are provided to a processing component 130, which may perform image reconstruction. The processing component 130 may be one or more general or application-specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid-state memory storage structures. Moreover, the memory 138 may be located at the acquisition system site and/or may include remote storage devices for storing data, processing parameters, and/or routines for tomographic image reconstruction, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data.

While the preceding discussion has treated the various exemplary components of the imaging system 110 separately, these various components may be provided within a common platform or in interconnected platforms. For example, the processing component 130, memory 138, and operator workstation 140 may be provided collectively as a general or special-purpose computer or workstation configured to operate in accordance with the aspects of the present disclosure. In such embodiments, the general- or special-purpose computer may be provided as a separate component with respect to the data acquisition components of the system 110 or may be provided in a common platform with such components. Likewise, the system controller 124 may be provided as part of such a computer or workstation or as part of a separate system dedicated to image acquisition.

The system of FIG. 2 may be utilized to acquire X-ray projection data (or other scan data for other modalities) for a variety of views about a vascularized region of interest of a patient to reconstruct images of the imaged region using the scan data. Projection (or other) data acquired by a system such as the imaging system 110 may be reconstructed as discussed herein to perform a tomographic reconstruction. Although the system of FIG. 2 shows a rotational subsystem 132 for rotating the X-ray source 112 and detector 122 about an object or subject, a CT system where an X-ray source and detector are held fixed and the object is rotated, as in a CT system used for non-destructive evaluation, is also envisioned.

With the preceding background and context discussion in mind, the present disclosure relates to using non-invasively acquired images to derive one or more localized vascular properties of interest. In particular, there may be substantial diagnostic power in assessing the state of blood flow in vessels, especially the coronary arteries when a subject is under exertion (stress). For example, this information can be used to provide patient-specific boundary conditions for a computational fluid dynamics model that incorporates this information with localized anatomical information, such as may be attained using cardiac computed tomography angiography (CTA), to estimate the pressure distributions in localized regions, such as the coronary arteries. For example, blockages can restrict blood flow, affecting pressure in view of localized obstructions, and thereby impact downstream tissue (e.g., limit blood flow to myocardium or brain tissue). Heart attacks and strokes are acute events that may result from such conditions. With this in mind, such patient-specific pressure distribution data, such as may be obtained for the coronary arteries, may be used to estimate fractional flow reserve (FFR) (e.g., the ratio of the distal to proximal pressures across a suspected lesion) or other vascular parameters for the vessel of interest. Such information can be used to assess the hemodynamic significance of a constriction in a coronary artery, and improve the diagnostic accuracy of a system for evaluating the severity of vessel constriction, and help guide subsequent therapeutic regimens.

In order to facilitate the acquisition of such information, the presently described approaches address a number of challenges so as to provide an improved assessment of vessel health. In particular, the present approach to vessel assessment uses deep-learning-based approaches (as discussed in greater detail below) to perform, separately or in combination, some or all of vessel segmentation, decalcification, Hounsfield unit (HU) scoring, and hemodynamic parameter estimation (e.g., Fractional Flow Reserve (FFR) estimation), with a goal of quantifying vessel function.

As may be appreciated, each of these problems is complex and may be addressed by designing a customized algorithm. Such algorithms would, to be sufficiently effective, necessarily contain dozens or even hundreds of parameters which would need to be tuned to ensure good performance. Such a process would be extremely labor intensive and might still result in algorithms that are biased in certain situations. As opposed to such customized algorithms, deep-learning networks, as may be embodied in a multi-layer artificial neural network, can automatically learn an extensive number of parameters that can be used to recognize patterns that occur in typical datasets and quantify how these patterns should be interpreted. Such deep-learning approaches greatly accelerate algorithm development, assuming good training data is available, but at the cost of not having full understanding of how a particular network operates. That is, the details of what makes a particular trained network work (such as the purpose of each weight or filter) may be unknown. The present approach employs deep-learning networks to perform some or all of the four tasks noted above, i.e., 1) segmentation, 2) decalcification, 3) HU intensity scoring, and 4) hemodynamic parameter estimation (e.g., FFR estimation).

Figure 3:
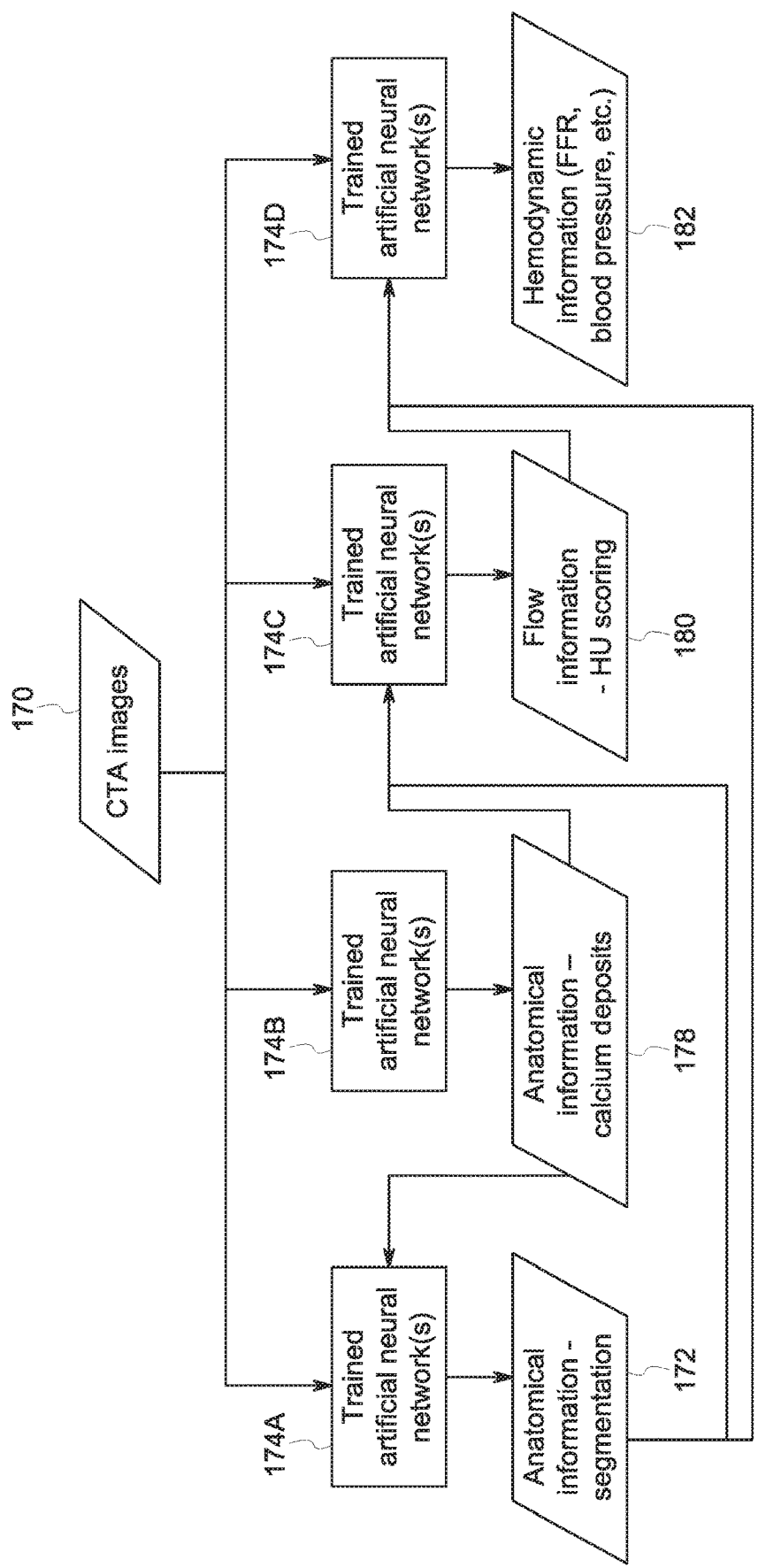
FIG. 3 depicts a block diagram of the use of one or more neural networks to process vascular images to estimate a hemodynamic parameter of interest, in accordance with aspects of the present disclosure.

With this in mind, and with respect to determining the functional impact of vascular blockages, both anatomical information and flow information are needed. This is represented in FIG. 3 at a generalized level. As discussed herein, vascular image data, such as may be obtained using CTA images 170 (which are typically acquired by imaging with a contrast (e.g., iodine) bolus being introduced into the vasculature of interest), can be used to derive anatomical information, such as performing segmentation of the vessels within the image data (172). With this in mind, the present approach may train and utilize a deep-learning algorithm, depicted as neural network 174A, to perform such a segmentation operation. In the depicted example, to facilitate explanation, each function or operation is depicted as being performed by a separate or different trained neural network 174. However, in practice, some or all of the described operations may be performed by a single neural network 174 or fewer neural networks than those disclosed. In such approaches, it may be appreciated that the depicted flow or interrelationship of outputs (e.g., segmentation, decalcification, HU scoring, hemodynamic parameter estimation) between functions may simply be accommodated by the various weightings and links between layers and neurons of the neural network(s), without an explicit provision of one output as an input to a separate operation.

In one example, the deep-learning algorithm for semantic segmentation classifies each voxel in a set of volumetric CT images to be either lumen or background or, in another implementation classifies each voxel in the images to be either lumen, fat, calcium or background. That is, the segmentation operation associates each voxel in the CT volumetric images with a label, one of which is associated with depicting lumen (i.e., vessel). The segmentation result can be used as segmentation information 172 for subsequent operations and/or can be used to construct or parameterize a computational fluid dynamics (CFD) model used to predict a vascular parameter of interest, such as FFR. Alternatively, the likelihood of a voxel in a set of volumetric CT images to be either lumen or background or, in another implementation, either lumen, fat, calcium or background, can be ascribed. In this context, a likelihood of 1 and 0 refer to absolute certainty that the voxel is comprised of a certain material or not, respectively.

As may be appreciated by those skilled in the art, the presence of calcium in the imaged region may make it difficult to accurately determine the size or scope of a blockage. For example, calcium deposits can often impair the visualization or exaggerate the magnitude of coronary blockages, making it difficult to make an accurate assessment of any particular blockage, thereby incurring false positives (classification of a blockage, when one is not actually present) requiring further follow up. As a result, another aspect of the present approach may utilize deep-learning approaches, depicted as neural network 174B, to remove the contribution of calcium deposits (output 178) to the image (i.e., decalcification), which may have the effect of improving the accuracy of other operations, such as the segmentation step (174A) noted above, which thus may improve the anatomical information derived from the image data 170. Similarly, the identification of calcium contribution 178 to the image may be useful in determining the flow information 180 e.g., HU scoring, as shown in FIG. 3.

With respect to flow information 180, this information can be gathered in many ways. In one approach discussed herein, the contrast intensity e.g., (HU intensity or scoring 180) is estimated at each segmented location within a coronary tree at one or more times. By way of example, a flow may be determined based on a spatial contrast intensity distribution, a process for which is described in U.S. Patent Application No. 2017/0325769, which is incorporated by reference herein in its entirety and for all purposes. This information can be used to estimate flow when combined with an estimate of the time-density profile input obtained from region-of-interest measurements near the origin of the vessel in question (e.g., in the aorta or left ventricle). Thus, calculation of the flow information (e.g., HU scoring 180) may in turn be based on the derived anatomical information 172 (e.g., segmented vessel(s)). In practice this may be accomplished using a neural network 174C or the appropriate functionality trained into a more comprehensively trained neural network.

Further, as discussed herein one or both of a blood pressure distribution or FFR distribution 182 may be derived using a suitable trained neural network 174D or a neural network trained to perform one or more of the functions noted above and to optionally leverage the anatomical segmentation information 172 and flow information 180 noted above. By using a trained neural network(s) 174D, such distributions may be derived without constructing or parameterizing a computational fluid dynamics (CFD) model.

As noted above, a key aspect to using neural networks to perform some or all of the functions mentioned above is the training of the respective neural network(s) 174. Factors relevant to successful training include: 1) access to good ground-truth data, and 2) effective network design choices, such as topology and loss function.

With respect to access to good ground-truth data, there are various ways to get access to a dataset that is passable as "ground truth", but many of these are extremely difficult to do, especially with respect to quantities that would be needed to train useful deep-learning algorithms. For example, with respect to the four problems noted above as being of interest in the context of vascular assessment, several problems with obtaining ground-truth data may exist.

In the case of decalcification (i.e., removing the effects of calcium from an image), it may be desirable to digitally replace the calcium in the tissue with fat or another soft tissue material with similar contrast. This methodology allows for the deep-learning network to learn how calcium is represented in the final images, allowing the network to learn about relevant artifacts such a calcium blooming resulting from non-linear partial volume effects. For a clinical exam there is no practical way to generate such an image as it would require surgically removing the calcium somehow and re-imaging while somehow ensuring that all other factors remain the same as the original scan (e.g., exactly the same heart phase, patient positioning, contrast distribution, etc.). This is not feasible for even a small data set, much less a data set large enough to train a deep-learning algorithm.

In the case of segmentation, obtaining ground-truth information would require a more accurate method of measuring the coronary (or other vascular) geometry. As mentioned above, this information can be ascertained using intravascular ultrasound (IVUS) or Optical Computed Tomography (OCT), but there are challenges associated with these approaches including registration of IVUS/OCT data to volumetric CT images and changes in the geometry due to cardiac phase, patient positioning, heart rate, level of patient stress, or other such factors. Furthermore, IVUS and OCT are invasive procedures in which measurements are acquired using a catheter positioned within the coronary vessel of interest. Hence, it is expensive to perform a large number of such exams needed for training of a deep-learning network, and introduces risk that is absent in non-invasive procedures.

In the case of Hounsfield unit (HU) scoring, independent and accurate measurement of the ground-truth contrast (e.g., iodine) density throughout the coronary tree at a particular instant of time during a coronary CT angiography (CTA) scan is simply not possible by any current method. Phantoms could be produced that would mimic the clinical scenario but would require a great deal of effort and would require a rich variety of vessel geometries and orientations to be clinically relevant, as well as a wide variety of scan settings and variation in cardiac geometry in order to cover the range of possible clinical images that might occur. Non-rigid motion may also be introduced if the goal were to closely represent the clinical scenario. Producing such phantoms physically would be a very expensive task and would still result in a limited range of modeled vessel geometries.

Lastly, in the case of hemodynamic parameter estimation, such as fractional flow reserve (FFR) estimation, it may be possible to train a deep neural network to predict a hemodynamic parameter of interest based on CTA images acquired of the patient and invasively measured ground-truth hemodynamic parameter values for a given patient. However, it would be necessary to collect such information in a large number of patients for training a neural network, which is not a feasible endeavor and again contemplates an invasive approach to measure ground-truth value(s) of interest. CTA images without corresponding ground-truth FFR information are available and plentiful and such images could be used to predict FFR using three-dimensional (3D) computational fluid dynamics (CFD) models. The clinical images and predicted FFR could be then be used for deep-learning algorithm training. However, the predicted FFR cannot reasonably be considered as ground truth. In particular, there are inaccuracies introduced by conventional lumen segmentation as well in estimation of coronary flow from CTA images. These inaccuracies in turn translate to inaccuracies in the predicted FFR through the CFD model, preventing such estimations from being useful as ground-truth values.

Thus, for each of the problems being addressed, it is not generally feasible to have a corresponding ground-truth value for given CTA images 170. In accordance with the present approach, this is addressed in two ways. CT simulation routines (i.e., software) which models the geometry of the CT scanner, the detector aperture, focal spot aperture, X-ray spectrum, X-ray physics, and so forth, are used with both analytic and digital phantoms (mathematical constructs of objects mimicking clinical anatomy) for which ground-truth values are explicitly known due to the images being the result of a simulation process for which all parameterization is known. That is, the generated synthetic images, unlike clinical images, are the result of known parameterization with respect to the represented anatomy (e.g., exact knowledge of the vessel and calcium morphology), contrast level, blood flow, and scanner geometry; therefore, these data can be associated with known ground-truth data.

These phantoms correspond to a large training image dataset and represent a variety of vessel geometries, percent stenosis, HU signal intensities, surrounding tissue (tissue proximal to the vessels and adjoining structures such a heart chambers), noise realizations, and so forth. In this manner, the CT simulation routines simulate the images that would be produced in a variety of clinical scenarios. Since the phantom and scan parameters are fully customizable, it is possible to simulate exactly what CTA image would result, for example, if calcium deposits were replaced by fat. Similarly, it is possible to fully control the iodine density in the vessel lumen and to simulate a wide variety of vessel geometries, plaque shapes, and other nearby structures. Taken together, this allows a large and varied ground-truth dataset to be generated for segmentation, decalcification, and HU scoring deep-learning applications. Importantly, the blurring caused by the finite resolution of the scanner and the reconstruction algorithm are accurately represented in this process.

With respect to ground-truth determination for FFR estimation, the pressure drop across the ground-truth lumen geometry can be predicted for a range of flow rates using 3D CFD calculations. The predicted pressure drop can be considered a viable ground truth since the geometry of the digital phantom is known exactly. Similarly, other ground-truth hemodynamic properties can be similarly determined based on the known lumen geometry and flow rates.

Figure 4:
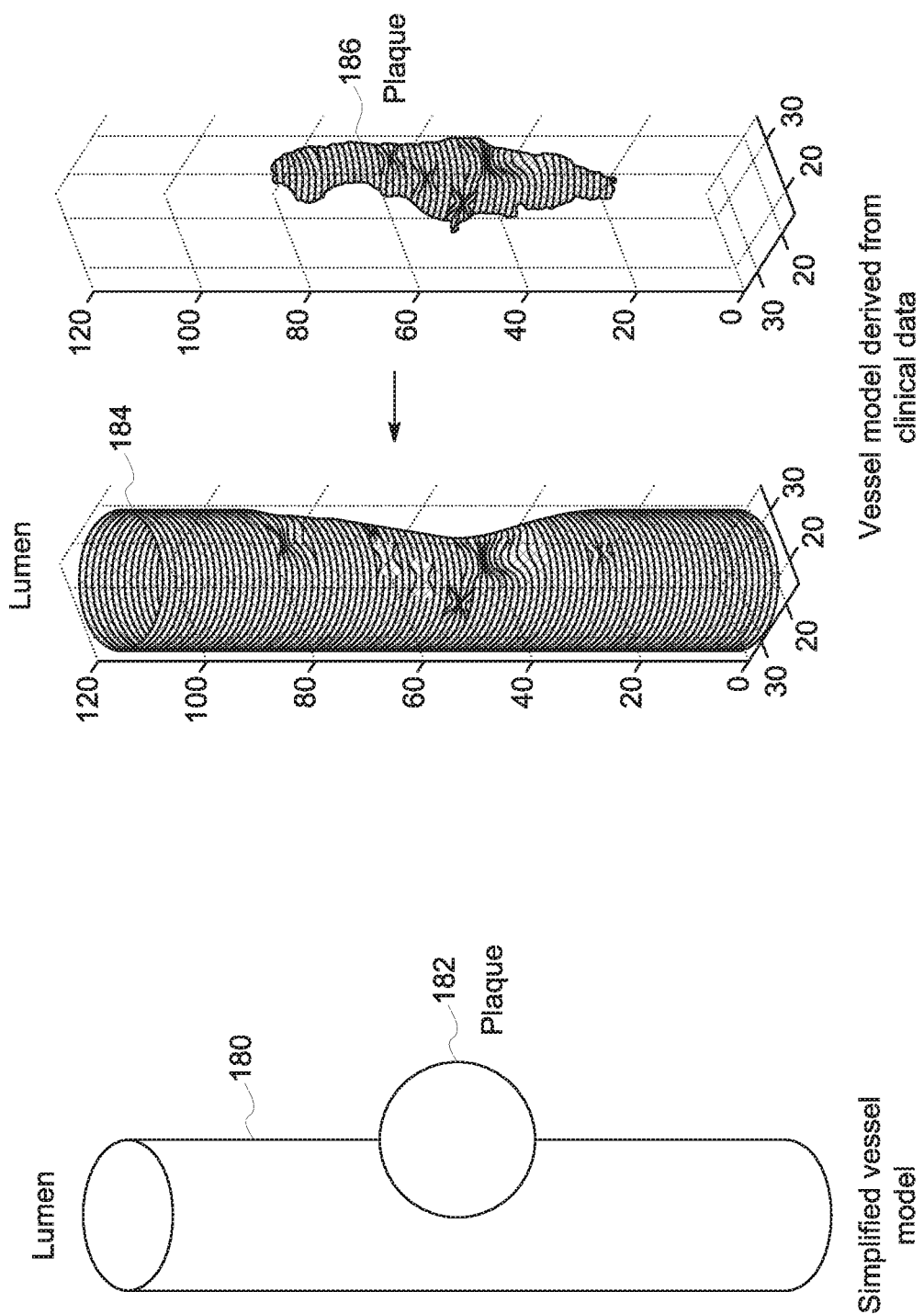
FIG. 4A depicts a rendering of a simplified vessel model, in accordance with aspects of the present disclosure.
FIG. 4B depicts a rendering of a vessel model derived from clinical data, in accordance with aspects of the present disclosure.

In one implementation the dataset is augmented with information derived from vessel models, as shown in FIGS. 4A and 4B, in which FIG. 4A depicts a simplified vessel model and FIG. 4B depicts a rendering of a vessel model derived from clinical data. The simplified vessel model shown in FIG. 4A comprises a lumen 180 and the plaque 182, whereby the density and composition of each of the lumen 180 and plaque 182 can be specified. In another implementation, the dataset is augmented with information derived from real life, i.e., clinical, data. The models derived from clinical data, as shown in FIG. 4B, comprise lumen 184 and the plaque 186, whereby the density and composition of each the lumen 184 and plaque 186 can be specified. In this manner the simulated images can be derived so as to correspond to the appearance of real vasculature, calcium deposits, and so on, imaged at a variety of different scan parameters and/or geometries. Information derived from simplified vessel models enable easy modification of model parameters for generation of the large dataset required for training a deep-learning network. Using information derived from clinical images improves the richness of the training data, whereas synthetic images generated from simplified geometric constructs, although useful, have limited applicability to actual vasculature (and, therefore, limited training value). Optionally, either model additionally comprises one or more of adjacent structures (e.g., heart chambers, surrounding lung, etc.), variability of the background material (e.g., fat, etc.), and variable contrast enhancement in the lumen from an injected contrast agent such as iodine. In an alternate approach, both sources of data may be used to train a deep-learning network. Additionally, synthetic images generated using one or more of simplified vessel models or vessel models derived from clinical data may be combined with clinical data for which ground truth information is known (e.g., vessel segments known to be free from calcium deposits) for training the deep-learning network.

Figure 5:
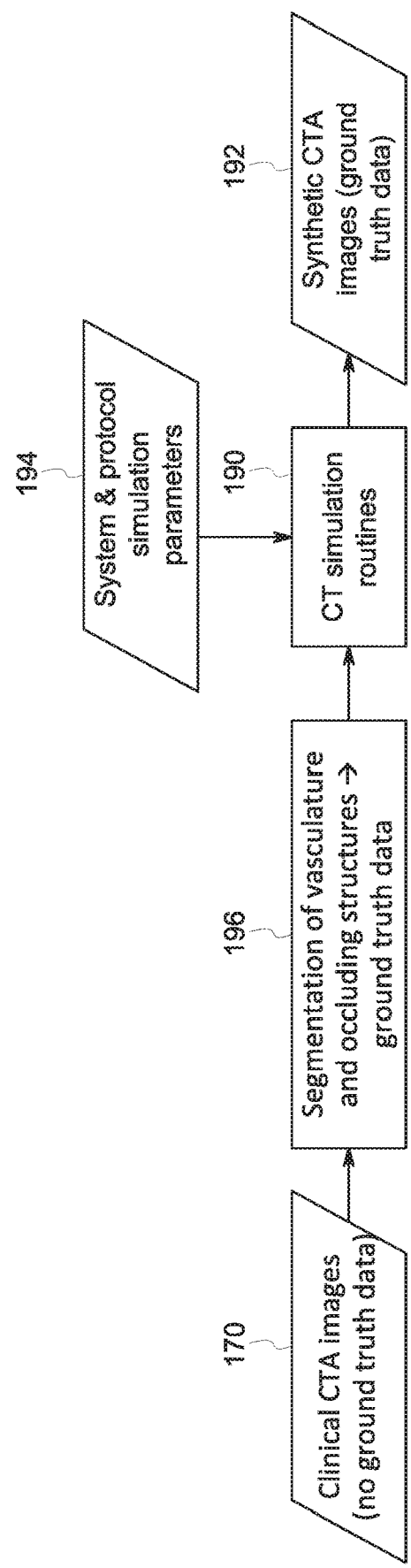
FIG. 5 depicts a process for generating synthetic images having known ground-truth values comprising one or more of vasculature and occluding structures for training one or more neural networks, in accordance with aspects of the present disclosure.

An example of this approach is illustrated in FIG. 5, which illustrates the use of clinical CTA images 170, for which no ground-truth data for the values to be estimated (e.g., localized flow rates, localized pressure distributions, fractional flow reserve, and so forth) are available in the context of the CTA images 170 alone. By way of example, these images are first segmented (step 196) to produce a geometric representation of the true underlying lumen geometry and that of each calcium deposit. Segmentation of other geometric features, such as plaque components, adjoining structures, etc., is also envisioned. These geometric representations can be voxelized (converted to or represented by volumetric representations where each voxel corresponds to a particular tissue type or combination of tissue types based on the voxel's location relative to the geometric representation), or characterized by polygonal surfaces, NURBS (non-uniform rational b-splines), or any number of other representations. These representations may not exactly match the original shapes of the true lumen and calcium, but they are sufficiently close that when taken together, a large series of these representations extracted from a large set of corresponding CTA image volumes are representative of the types of shapes commonly found in clinical practice. The fact that they do not match exactly may be attributed to the observation that segmentation is a difficult problem, especially in the presence of noise, resolution limits, and other image non-idealities. Nevertheless, an exact match is not necessary as these representations (explicitly defined in accordance with the present approach) become the ground-truth shapes which are then used as one input to a set of CT simulation routines 190 which construct synthetic CTA images 192 based on the observed geometry of the clinical CTA images 170 and based on one or more specified system and protocol simulation parameters 194 (e.g., geometry of the CT scanner, the detector aperture, focal spot aperture, operating voltage of the X-ray tube, electron beam current, X-ray beam filtration, X-ray spectrum, X-ray physics, and so forth) that mimic the hardware used to acquire the clinical images 170.

Because the inputs to and operation of the CT simulation routines 190 are all known, the resulting synthetic CTA images 192 have corresponding, known ground-truth value(s) for the parameter(s) of interest. The synthetic CTA images 192 derived from clinical CTA images, but having known ground-truth values, may then be used in the training of one or more neural networks 174 (FIG. 3) as discussed herein. Further, to enrich the dataset, the geometric models derived from clinical data can be modified in a number of ways. For example, they can be scaled, rotated, and warped. An arbitrary contrast level can be used which may be unrelated to the contrast in the original CTA image from which the shapes were derived. Moreover, a spatially-varying contrast level along the length of the vessel can be defined for the vasculature. The noise level and other scan parameters can also be controlled independently.

While the preceding relates to generating and using synthetic image data to train neural networks for vessel assessment, as noted above, network design is also a factor. With respect to network design choices, in one implementation convolutional neural network design choices for a deep-learning algorithm for segmentation (e.g., neural network 174A) include the use of an encoder-decoder architecture, such as U-Net, or an architecture which uses dilated/atrous convolution to allow for exponential increase in field of view without decrease of spatial dimensions from the use of pooling layers as in the first architecture. Both deep-learning architectures may be effective for many semantic segmentation tasks. The loss function for a respective segmentation can be cross entropy, DICE, or mean squared error.

With respect to HU scoring using a deep-learning algorithm (e.g., neural network 174C), a convolutional neural network architecture may be employed that contains only the contracting path as typically used in regression and classification tasks. In one such implementation, to mitigate the problems of reduced sampling, the original reconstructed volume is upsampled to a denser spatial sampling. In addition, the geometry of the resampling grid may be warped to follow the course of each coronary branch such that the output of the resampling (e.g., upsampling) has the vessel centerline running through the middle of the volume.

With respect to decalcification, in one embodiment the input to the neural network (e.g., neural network 174B) is the original CTA images 170 and the output 178 is the predicted difference between the original images 170 and a predicted or estimated image based on the replacement of the calcium by fat. The fat-predicted image may then be generated by subtraction. This approach may be preferable to outputting the fat-predicted image directly as there is the potential for information loss at the low-resolution scales of the U-net. Further, this approach allows for the preservation of network resources for the task of estimating the (localized) calcium impact rather than preserving background details in the full image. The loss function for the decalcification can be mean squared error or another similar metric.

With respect to estimation of hemodynamic parameters using a trained neural network 174D, in an implementation in which fractional flow reserve (FFR) is estimated, the FFR prediction neural network may have available as inputs the ground-truth pressure drop at each flow rate from a 3D CFD model as described above. In one such approach, the input image volume for the FFR pressure drop may be reformatted as described above with respect to HU scoring such that the vessel is positioned in the middle of the volume and may be cropped to include a limited section of the vessel (such as a region around a stenosis). This reduced or limited image volume is used as an input to a half-U-net or other similar network architecture with the outputs being the pressure drop that would be expected at each of the flow rates for which ground truth is known. The loss function penalizes the discrepancy from the ground-truth pressure drop at each flow rate. The expected pressure drop at an arbitrary flow rate within the ground-truth range can be inferred using a simple (e.g. quadratic) model or a smooth interpolation. In another embodiment, the image volume is not restricted as described above. Rather, the 3D CFD model is used to extract the total pressure drop at each flow rate. The reason for using the total pressure drop is as follows. The change in static pressure includes the pressure drop/rise due to flow acceleration/deceleration, such as within and just downstream of a stenosis, in addition to frictional loss at the walls. When the image volume is not restricted, the static pressure drop may not be representative of the pressure drop due to the stenosis. The total pressure drop, on the other hand, includes only the losses, frictional loss at the wall and any inertial losses due to recirculation and/or turbulence. Thus, it is a suitable pressure drop to track when the image volume is not restricted. The pressure drop due to a stenosis is not only the result of losses within the stenosis, but also losses downstream of the stenosis. The downstream losses can be the result of flow recirculation, turbulence and wall friction. These losses occur even when the vessel downstream of the stenosis is normal. To predict these losses using deep learning, the velocity profile shape at the inlet to the image volume and the flow rate are provided as inputs to a half U-net or similar network architecture, in addition to the image volume itself. The outputs are the total pressure drop across the image volume and the velocity profile shape at the image volume outlet. The velocity profile shape could be in the form of a 3D profile (i.e., velocity as a function of x, y and z co-ordinates) or a 1D number characteristic of the shape (e.g., maximum velocity/average velocity). The trained network can then be applied in a sequential manner, upstream to downstream to the stenosis, to obtain the pressure drop along a vessel segment including the stenosis. In an additional embodiment, deep learning is used to obtain parameters in a 1D blood flow model, which is then used to predict the pressure distribution. The 1D momentum conservation equation has the following form:

$$\alpha \frac{\partial}{\partial z}\left(\frac{Q^2}{A}\right) + \frac{A}{\rho}\frac{\partial p}{\partial z} - 2\pi\frac{\mu}{\rho}s'\frac{Q}{A} = 0 \quad (1)$$

where Q is the volumetric flow rate, A is the cross-sectional area, p is the pressure. and $\alpha$ and s' are parameters related to the velocity profile shape. The parameter s' is related to the wall frictional loss. The parameter $\alpha$ is defined as $$\alpha = \frac{A\int u_z^2 dA}{Q^2},$$

where $u_z$ is the velocity in the z direction.

These parameters may be estimated by assuming a parabolic velocity profile; however, this assumption may impact the accuracy of the pressure distribution predicted by the 1D model. To improve accuracy, these parameters may instead be obtained using deep learning. From the 3D CFD model, this parameter may be obtained at multiple locations along the length of the image volume such that the term $$2\pi\frac{\mu}{\rho}s'\frac{Q}{A}$$

matches the wall frictional loss predicted by the 3D model. Similarly, the parameter $\alpha$ is also obtained at multiple locations along the length of the image volume. A half U-net or similar network architecture is then trained with the image volume, flow rate and velocity profile shape at the image volume inlet as inputs and the outputs being the values of the parameters $\alpha$ and s' at multiple locations along the length of the image volume and the velocity profile shape at the image volume outlet. The trained network together with the 1D model can then be used to predict the pressure distribution.

As may be appreciated from the present approach, one possible application of the presently described approach is quantifying FFR. While fractional flow reserve can be measured directly using a pressure wire that is threaded through the coronary artery of a patient, it may instead be beneficial to obtain localized estimates of FFR in a non-invasive manner using imaging, which the present approach facilitates.

Technical effects of the invention include training one or more neural networks for vascular vessel assessment using synthetic image data for which ground-truth data is known. In certain implementations, the synthetic image data may be based in part, or derived from, clinical image data for which ground-truth data is not known or available. Neural networks trained in this manner may be used to perform one or more of vessel segmentation, decalcification, Hounsfield unit scoring, and/or estimation of a hemodynamic parameter.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for processing a vascular image volume, comprising:
   acquiring one or more vascular image volumes using an imaging system;
   providing the one or more vascular image volumes to one or more neural networks, wherein the one or more neural networks are trained using at least one or more synthetic images to perform:
   removing the effects of calcium in all or part of the vascular image volumes;
   segmenting one or more vessels within the vascular image after the effects of calcium are removed; and
   deriving one or more hemodynamic parameters for all or part of the segmented vessels.

2. The method of claim 1, wherein the vascular image volume comprises a computed tomography angiogram (CTA).

3. The method of claim 1, wherein the one or more synthetic images have known ground-truth values for one or more features or parameters of interest.

4. The method of claim 1, further comprising:
   determining a contrast level for one or more sections of the segmented vessels, wherein determining a contrast level comprises determining a Hounsfield unit estimate for one or more positions along the segmented vessels.

5. The method of claim 1, wherein the one or more hemodynamic parameters comprise a fractional flow reserve.

6. An imaging system comprising:
   a memory encoding processor-executable routines;
   a processing component configured to access the memory and execute the processor-executable routines, wherein the routines, when executed by the processing component, cause the processing component to:
   acquire one or more vascular image volumes;
   provide the one or more vascular image volumes to one or more neural networks, wherein the one or more neural networks are trained using at least one or more synthetic images to perform:
   segmenting one or more vessels within the vascular image volumes;
   determining a contrast level for one or more sections of the segmented vessels, wherein determining a contrast level comprises determining a Hounsfield unit score for one or more positions along the segmented vessels; and
   deriving one or more hemodynamic parameters for all or part of the segmented vessels.

7. The imaging system of claim 6, wherein the imaging system comprises a computed tomography system.

8. The imaging system of claim 6, further comprising:
   removing the effects of calcium in all or part of the vascular image volumes, wherein the one or more vessels are segmented after the effects of calcium are removed.

9. The imaging system of claim 6, wherein the one or more synthetic images have known ground-truth values for one or more features or parameters of interest.

10. The imaging system of claim 6, wherein the one or more hemodynamic parameters comprise a fractional flow reserve.

11. A method for processing a vascular image volume, comprising:
    acquiring one or more vascular image volumes using an imaging system;
    providing the one or more vascular image volumes to one or more neural networks, wherein the one or more neural networks are trained using at least one or more synthetic images to perform:
    segmenting one or more vessels within the vascular image volumes;
    determining a contrast level for one or more sections of the segmented vessels, wherein determining a contrast level comprises determining a Hounsfield unit estimate for one or more positions along the segmented vessels; and
    deriving one or more hemodynamic parameters for all or part of segmented vessels using a computational fluid dynamics model.

12. The method of claim 11, further comprising:
    removing the effects of calcium in all or part of the vascular image volumes, wherein the one or more neural networks are trained to perform one or more of segmenting vascular vessels within an image volume, remove the effects of calcium in all or part of the images, determine a Hounsfield unit score corresponding to segments of vascular vessels within the images, or estimate a hemodynamic parameter for the vascular vessels within the images.

* * * * *